(12) United States Patent
Itsuji

(10) Patent No.: US 7,759,946 B2
(45) Date of Patent: Jul. 20, 2010

(54) WAVEGUIDE, AND DEVICE AND DETECTION METHOD USING THE SAME

(75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 699 days.

(21) Appl. No.: 11/573,507

(22) PCT Filed: Aug. 31, 2006

(86) PCT No.: PCT/JP2006/317695

§ 371 (c)(1),
(2), (4) Date: Feb. 9, 2007

(87) PCT Pub. No.: WO2007/029757

PCT Pub. Date: Mar. 15, 2007

(65) Prior Publication Data

US 2009/0219511 A1 Sep. 3, 2009

(30) Foreign Application Priority Data

Sep. 5, 2005 (JP) ............... 2005-256655

(51) Int. Cl.
*G01R 27/04* (2006.01)
*G01R 27/32* (2006.01)
(52) U.S. Cl. ...................... 324/639; 324/637
(58) Field of Classification Search ........... 324/637, 324/639
See application file for complete search history.

(56) References Cited

U.S. PATENT DOCUMENTS

| | | | |
|---|---|---|---|
| 5,109,442 A | 4/1992 | Klainer et al. | 385/12 |
| 5,623,145 A | 4/1997 | Nuss | 250/330 |
| 5,710,430 A | 1/1998 | Nuss | 250/358.1 |
| 6,100,703 A * | 8/2000 | Davidov et al. | 324/631 |
| 6,328,932 B1 | 12/2001 | Carter et al. | 422/82.06 |
| 6,873,165 B2 * | 3/2005 | Lee et al. | 324/750 |
| 7,113,143 B2 * | 9/2006 | Minemura | 343/870 |

(Continued)

FOREIGN PATENT DOCUMENTS

DE 102 57 225 4/2004

(Continued)

OTHER PUBLICATIONS

K. Wang, et al., "Metal Wires for Terahertz Wave Guiding", Letters to Nature, vol. 432, pp. 376-379 (Nov. 18, 2004).

(Continued)

*Primary Examiner*—Jeff Natalini
(74) *Attorney, Agent, or Firm*—Fitzpatrick, Cella, Harper & Scinto

(57) ABSTRACT

A waveguide includes a single line formed by a conductive material for propagating an electromagnetic wave including at least a part of a frequency band of 30 GHz or more and 30 THz or less, a first dielectric member covering the single line, and a second dielectric member covering the single line. A gap is provided between the first dielectric member and the second dielectric member. The electromagnetic wave which propagates from the single line covered by the first dielectric member to the single line covered by the second dielectric member, when propagating through the single line at the gap, is interactable with a specimen to be disposed at the gap.

9 Claims, 12 Drawing Sheets

U.S. PATENT DOCUMENTS

| | | | |
|---|---|---|---|
| 7,511,512 B2 * | 3/2009 | Sekiguchi | 324/638 |
| 7,608,826 B2 * | 10/2009 | Itsuji | 250/341.1 |
| 7,682,567 B2 * | 3/2010 | Itsuji et al. | 422/82.11 |
| 2004/0058339 A1 | 3/2004 | Nagel et al. | 435/6 |
| 2004/0058343 A1 * | 3/2004 | MacDonald | 435/6 |
| 2005/0151690 A1 | 7/2005 | Minemura | |
| 2007/0108382 A1 | 5/2007 | Itsuji | 250/330 |
| 2008/0048678 A1 * | 2/2008 | Kurosaka et al. | 324/639 |

FOREIGN PATENT DOCUMENTS

| | | |
|---|---|---|
| JP | 8-320254 | 12/1996 |
| JP | 2001-174406 | 6/2001 |
| WO | WO 2006/019776 | 2/2006 |

OTHER PUBLICATIONS

"Nature", vol. 432, pp. 376-379, 2004.

Chinese Office Action dated Apr. 28, 2010, in related corresponding Chinese Patent Appln. No. 200680032300.1 (with English translation).

* cited by examiner

WAVEGUIDE, AND DEVICE AND DETECTION METHOD USING THE SAME

TECHNICAL FIELD

The present invention relates to a waveguide technique for propagating electromagnetic waves in a region from the millimeter wave to the terahertz wave. Further, the present invention relates to an inspection device which performs analysis and identification of physical properties of a specimen by using the electromagnetic waves in the region from the millimeter wave to the terahertz wave.

BACKGROUND ART

In recent years, a non-destructive inspection technique using a high frequency electromagnetic wave (hereinafter refer to as "terahertz wave") having an arbitrary band in the region from the millimeter wave to the terahertz wave (from 30 GHz to 30 THz) has been developed. It is known that there exist many absorption lines of various substances including biomolecules in the terahertz wave region. Therefore, as an application field of this frequency region, there is a technique for performing the imaging as a safe fluoroscopic inspection device, instead of the X-ray fluoroscopic inspection device. Further, the application field of this frequency region also includes a spectroscopic technique for examining the bonded state of molecules by obtaining an absorption spectrum and a complex dielectric constant in a substance. Further, an analysis technique of biomolecules, and a technique for evaluating the carrier concentration and mobility, or the like, are also expected as the application field of this frequency region.

As an inspection device in which a terahertz wave is used, a constitution as shown in FIG. 21 is disclosed (Japanese Patent Application Laid-Open No. 8-320254). As shown in FIG. 21, this inspection device is constituted to irradiate an object with a terahertz wave propagated through space, and to thereby measure constituent materials of the object on the basis of changes in the propagation state of the wave transmitted from the object.

However, in general, the terahertz wave is strongly absorbed by moisture. For this reason, when the terahertz wave is propagated in the atmosphere, as in the case of Japanese Patent Application Laid-Open No. 8-320254, the terahertz wave is greatly attenuated by the absorption due to moisture in the atmosphere. Thus, it is desired to detect a specimen by using a technique in which the electromagnetic wave is confined in a certain region so as to be transmitted, by the use of a waveguide technique, for example, an optical fiber waveguide, such as used in many electromagnetic wave techniques and optoelectronic techniques, in order to reduce the attenuation of the terahertz wave. It is shown that the terahertz wave is propagated through a single line path which is formed by a conductor so as to serve as a fiber-shaped waveguide for propagating the terahertz wave ("Nature", vol. 432, p 376-379, 2004).

Further, for detecting a specimen by using the fiber waveguide without the use of the terahertz wave range, there is proposed an optical fiber type specimen inspection device for measuring a trace of specimen in high sensitivity (Japanese Patent Application Laid-Open No. 2001-174406). As shown in FIG. 19, this specimen inspection device is constituted such that optical fiber waveguides are arranged so as to face each other with a certain gap. On the end surface of this fiber waveguide, materials having different refractive indexes are periodically arranged so that a resonance structure is formed. Thereby, a specimen which exists in the gap can be measured in high sensitivity.

A case where the waveguide technique using the optical fiber as disclosed by Japanese Patent Application Laid-Open No. 2001-174406 is applied to the terahertz wave is considered. In this case, the optical fiber waveguide is formed only by dielectric materials. Thus, depending upon the materials to be used, the propagation characteristic of the terahertz wave is affected by the frequency dependence of physical properties of the materials. Specifically, when the terahertz wave has a certain frequency region, it is conceivable that the propagation loss and dispersion characteristic of the terahertz wave are changed in accordance with frequency, and hence, the propagation waveform of the terahertz wave is greatly changed during the process of propagation in the waveguide. For this reason, such optical fiber waveguide is undesirable as a waveguide for propagating the terahertz wave. As a result, there is a need for a waveguide having more excellent propagation characteristics.

Further, in the specimen inspection device disclosed by Japanese Patent Application Laid-Open No. 2001-174406, it is difficult to make the device constitution small, because the optical fiber waveguides need to be arranged so as to face with each other, and an external mechanism for such arrangement is needed.

DISCLOSURE OF THE INVENTION

In view of the above described problems, according to the present invention, there is provided a waveguide for use in detection of physical properties of a specimen, including:

a single line which is formed by a conductive body capable of propagating an electromagnetic wave including a frequency band of 30 GHz to 30 THz, and a dielectric member which covers the single line, wherein the dielectric member has a gap for detecting the physical properties of the specimen.

Further, according to the present invention, there is provided a device for use in for detection of physical properties of a specimen, including:

a waveguide including a single line formed by a conductive body which is capable of propagating an electromagnetic wave including a frequency band of 30 GHz to 30 THz, and a dielectric member covering the single line, the dielectric member having a gap for detecting the physical properties of the specimen; and a detection part for detecting the electromagnetic wave propagated through the waveguide.

Further, according to the present invention, there is provided a specimen detecting method for detecting physical properties of a specimen, including:

a step of preparing a waveguide provided with a single line formed by a conductive body which is capable of propagating an electromagnetic wave included in a frequency band from 30 GHz to 30 THz, and with a dielectric member covering the single line, the dielectric member having a gap for detecting the physical properties of the specimen;

a step of arranging the specimen in the vicinity of the gap of the waveguide; and a step of detecting the electromagnetic wave propagated through the waveguide.

The waveguide according to the present invention is constituted by a single line formed by a conductor, and a dielectric member which has a gap and which covers the single line. With such constitution, it is possible to provide a waveguide having low dispersion propagation characteristics. Further, by inserting a specimen into this gap, it is possible to simply detect the physical properties of the specimen.

BEST MODE FOR CARRYING OUT THE INVENTION

Figure 1:
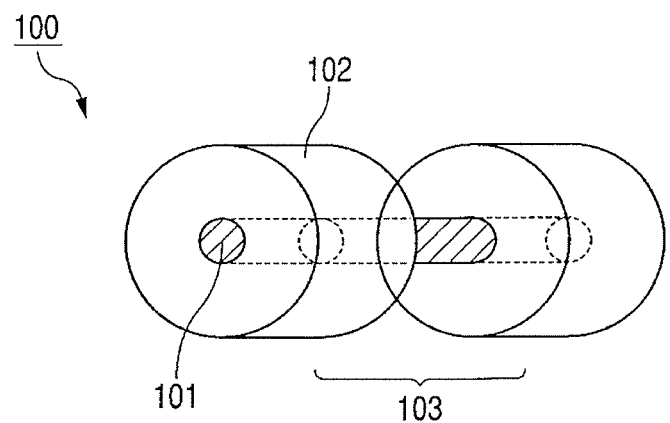
FIG. 1 is a schematic view showing a waveguide according to the present invention.

In the following, the best mode for carrying out the present invention is described with reference to accompanying drawings. The same elements are denoted by the same reference numerals in the figures.

(Outline of Waveguide)

FIG. 1 is a schematic view of a waveguide according to the present invention. As shown in FIG. 1, a waveguide 100 according to the present invention is constituted by a single line 101 and a dielectric member 102 covering the single line. The dielectric member 102 has a gap portion 103.

The single line 101 is a single lead wire constituted by a conductor. In FIG. 1, the single line 101 has a cylindrical shape, but the shape of the single line is not limited to this shape. For example, the single line 101 may have a polygonal shape.

The dielectric member 102 is constituted by a dielectric. The dielectric material used for the dielectric member 102 in the present invention preferably has a characteristic which is transparent to electromagnetic waves to be used. In FIG. 1, the dielectric member 102 has a cylindrical shape, but the shape of the dielectric member is not limited to this shape. For example, the shape of the dielectric member 102 may be a polygonal shape or a substrate-like shape. Further, the dielectric member 102 is preferably dimensioned such that the electromagnetic waves propagated through the waveguide 100 are distributed in the waveguide 100. The reason for this is to suppress the external influence on the electromagnetic waves propagated through the waveguide 100. It is known that the electromagnetic field distribution of the electromagnetic waves propagated through the single line 101 is the same as the electromagnetic field distribution in a coaxial waveguide. For example, a case where the cylindrical dielectric member 102 is used, as shown in FIG. 1, is considered. According to calculation, when the distance from the interface between the single line 101 and the dielectric member 102 to the external peripheral surface of the dielectric member 102 is set to half the wavelength or more, the electromagnetic field of the electromagnetic waves propagated through the waveguide 100 is distributed in the dielectric member 102. Further, a case where the electromagnetic waves propagated through the waveguide 100 have arbitrary frequency regions, is considered. In this case, the distance from the interface between the single line 101 and the dielectric member 102 to the external peripheral surface of the dielectric member 102 is secured to half the wavelength of the lowest frequency or more in the frequency regions occupied by the electromagnetic waves.

(Gap in Dielectric Member)

Figure 15:
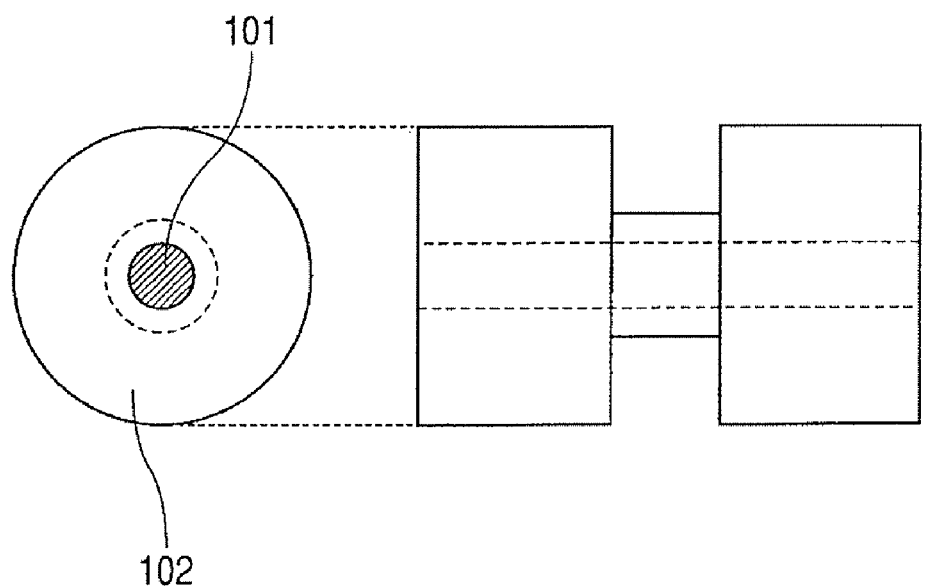
FIG. 15 is a schematic view showing an example of a shape of the gap portion.

As shown in FIG. 1, the waveguide 100 according to the present invention has the gap portion 103 in a part of the dielectric member 102. In FIG. 1, the dielectric coat of the gap portion 103 is eliminated, and the single line 101 is exposed. When the dielectric member 102 and the gap portion 103 have different refractive indexes, the propagation state of the electromagnetic waves propagated through the waveguide 100 is changed in the gap portion 103. Thus, by utilizing the change in the propagation state of the electromagnetic waves, which results from the difference in refractive indexes in the gap portion 103, it is possible to perform control of the signal, for example, to selectively eliminate and transmit a part of the frequency components of the electromagnetic waves. FIG. 1 shows a constitution in which the gap portion 103 is provided in a part of the dielectric member 102, but the method for forming the gap portion is not limited to the method for eliminating the dielectric. It is only necessary that a region where the refractive index is changed exists in the propagation path of the electromagnetic waves. Thus, for example, a constitution in which a material different from the dielectric member 102 is filled in the gap portion 103 may also be applied. Further, as shown in FIG. 15, a constitution in which all the dielectric of the gap portion 103 is not eliminated but a part of the dielectric is left, may also be applied. Even in such a case, the average refractive index in the gap portion 103 is changed, thereby enabling the propagation state of electromagnetic waves to be changed.

Figure 16:
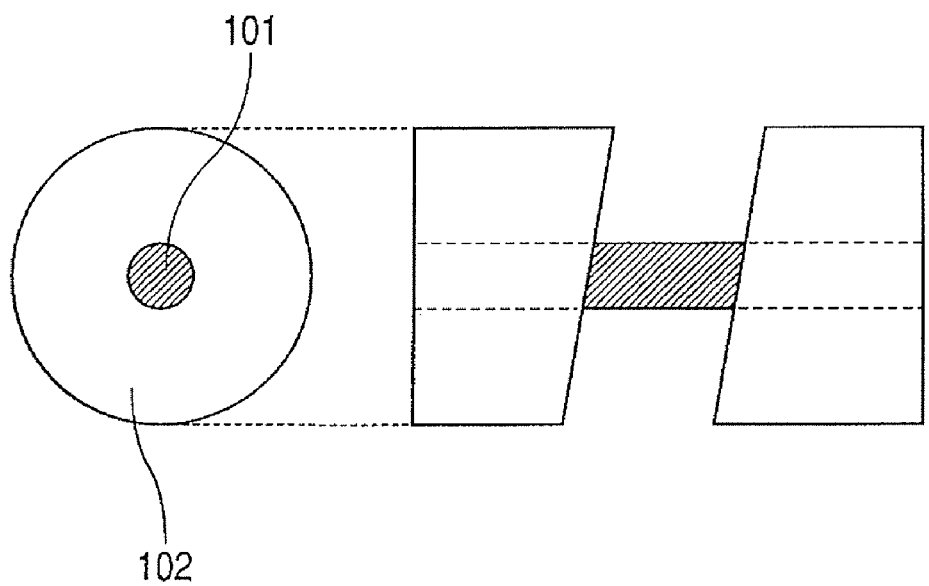
FIG. 16 is a schematic view showing another example of a shape of the gap portion.
Figure 17:
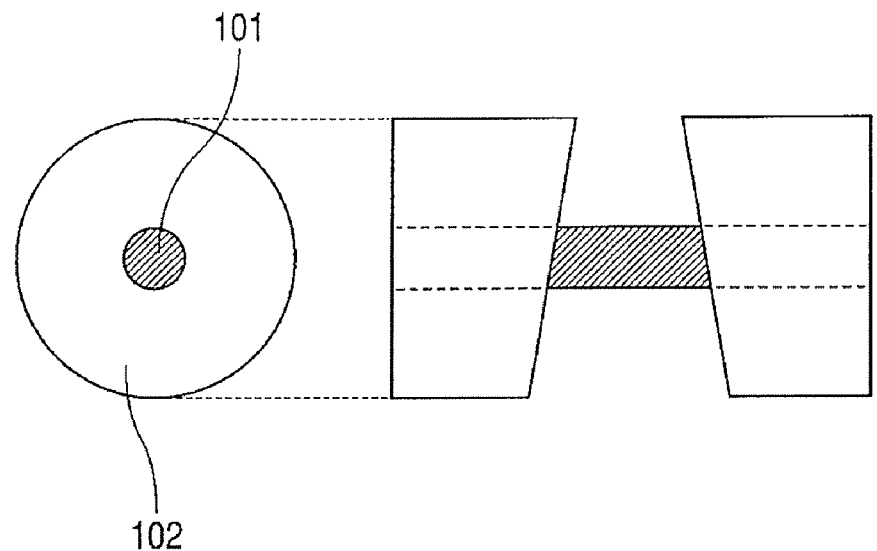
FIG. 17 is a schematic view showing another example of a shape of the gap portion.
Figure 18:
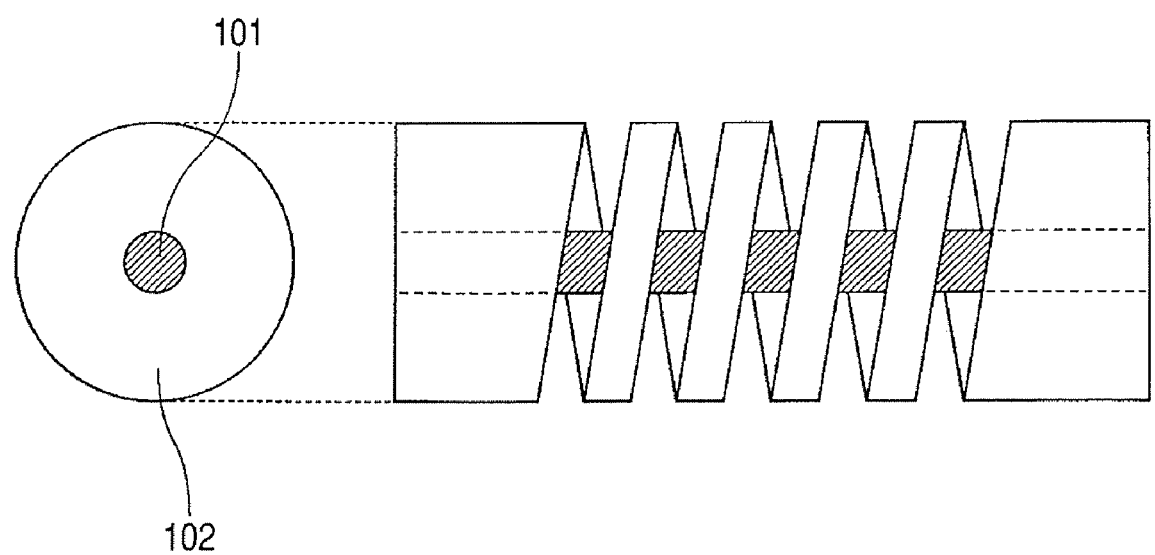
FIG. 18 is a schematic view showing another example of a shape of the gap portion.
Figure 19:
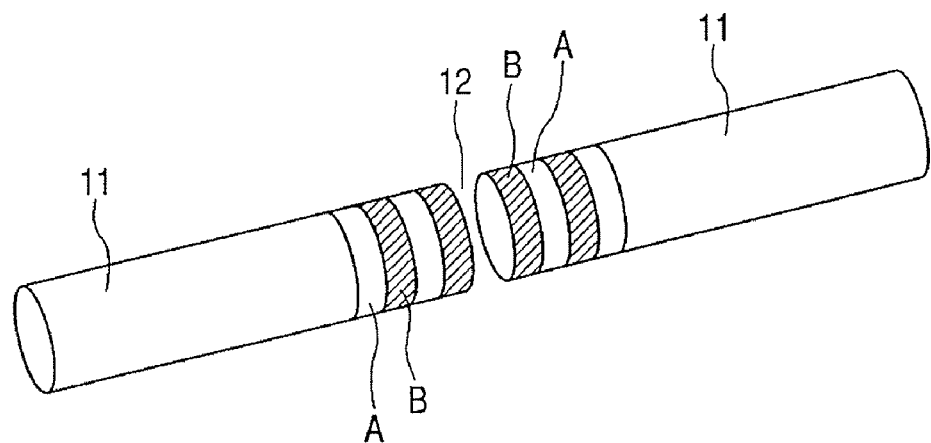
FIG. 19 is a schematic diagram for explaining an example of the prior art relating to an inspection element using an the optical fiber.
Figure 20:
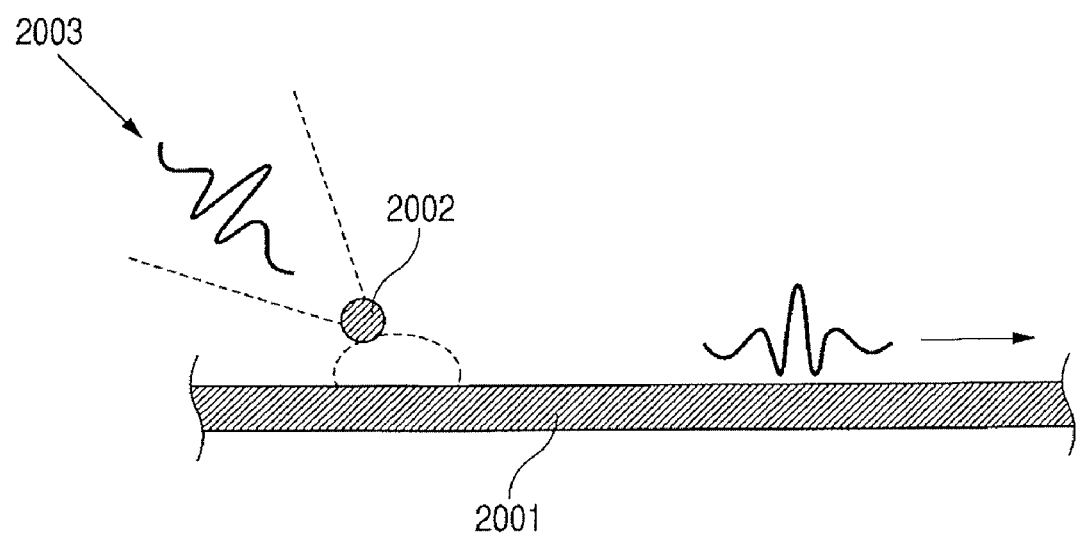
FIG. 20 is a schematic diagram for explaining an example of the prior art relating to a waveguide using a single line.
Figure 21:
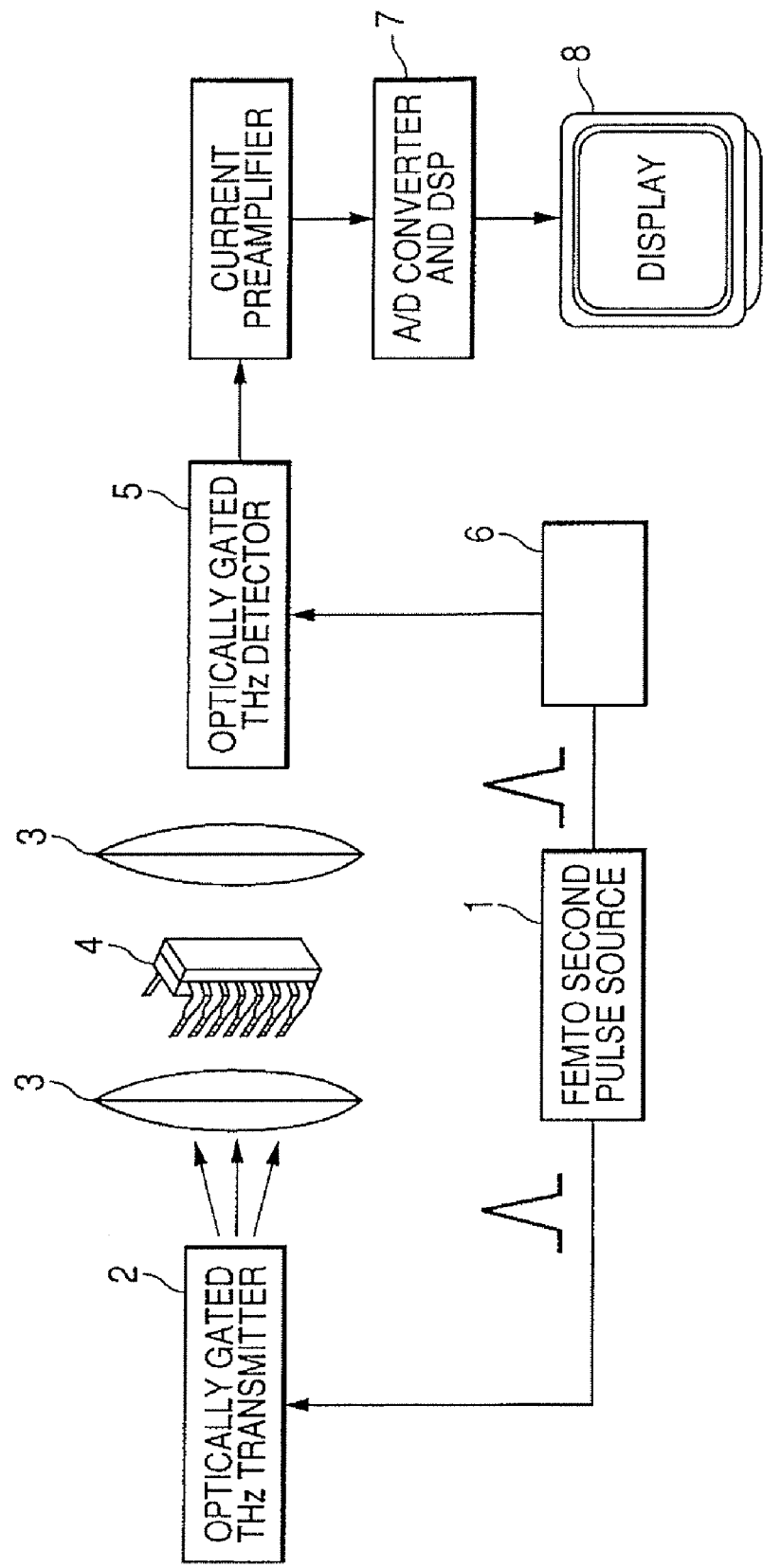
FIG. 21 is a schematic diagram for explaining an example of the prior art relating to an inspection device using a spatial optical system.

Further, in FIG. 1, the cross section of the dielectric members 102 which are disposed opposite to each other via the gap portion 103, is formed perpendicular to the longitudinal direction of the single line 101. However, the constitution in the gap portion is not limited to this arrangement. For example, as shown in FIG. 16, a constitution in which the cross section of the dielectric members 102 is inclined with respect to the longitudinal direction of the single line 101, may also be applied. Further, as shown in FIG. 17, the cross sections of dielectric members 102 may also form a tapered shape. Further, the cross sections of dielectric members 102 as described above are planar, but a part of or all of the cross sections of the dielectric members 102 may be spherical, rough or polygonal. Further, as shown in FIG. 18, the dielectric may also be spirally eliminated. Further the interval in the spirally eliminated portion may not be fixed, but may also be irregular in part or changed at a fixed ratio.

Further, it is preferred that the gap portions are arranged regularly in the waveguide. However, all the gaps need not be regularly arranged. The state where a part of the gaps are regularly arranged is effective. Further, the gap portion may also be constituted such that in the state where the gaps are regularly arranged, the regularity of the arrangement is intentionally disturbed. Thereby, the wavelength selectivity can be obtained. The periodic arrangement means the arrangement in which the gaps are arranged at certain intervals of wavelength. The self-similar arrangement means a constitution which is right and left symmetric to a cross section in a waveguide, when seen from the cross section.

(Constitution of Sensor Device)

Figure 2:
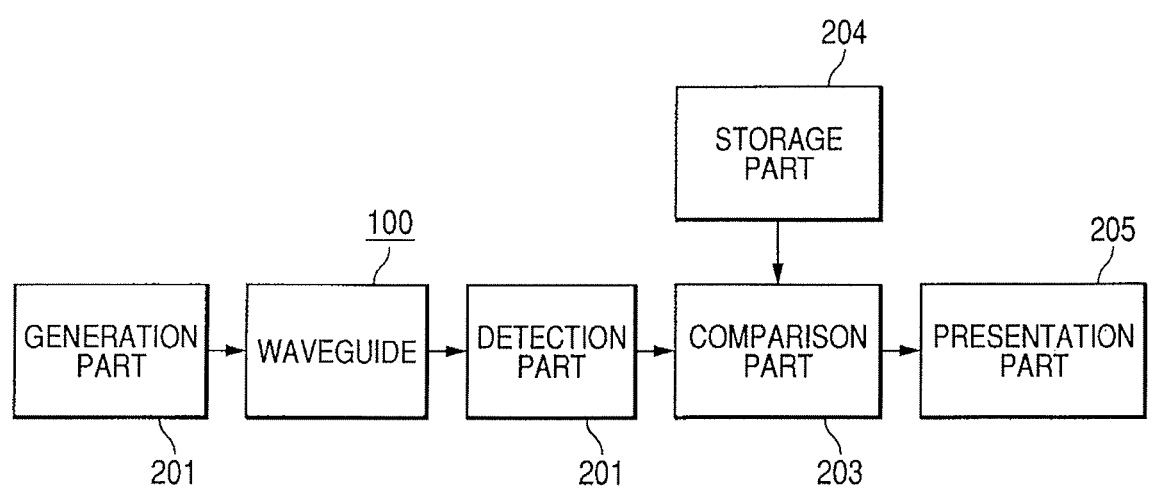
FIG. 2 is a schematic diagram for explaining a sensor device for measuring physical properties of a specimen according to the present invention.

FIG. 2 is a schematic diagram when the above described waveguide is applied as a sensor device for measuring physical properties of a specimen. As shown in FIG. 2, the device according to the present invention is constituted by a generation part 201, a waveguide 100, a detection part 202, a comparison part 203, a storage part 204, and a presentation part 205.

The generation part 201 has a function to generate a high frequency electromagnetic wave used in the device, for example, a terahertz wave, and to enable the electromagnetic wave to be coupled to the waveguide 100 and to be propagated. The generation part 201 may be constituted so as to be integrated with the waveguide 100, or may be constituted so as to generate the high frequency electromagnetic wave outside the waveguide 100, and to couple the generated electromagnetic wave to the waveguide 100.

(Generating Means and Coupling Means of Sensor Device)

Figure 4:
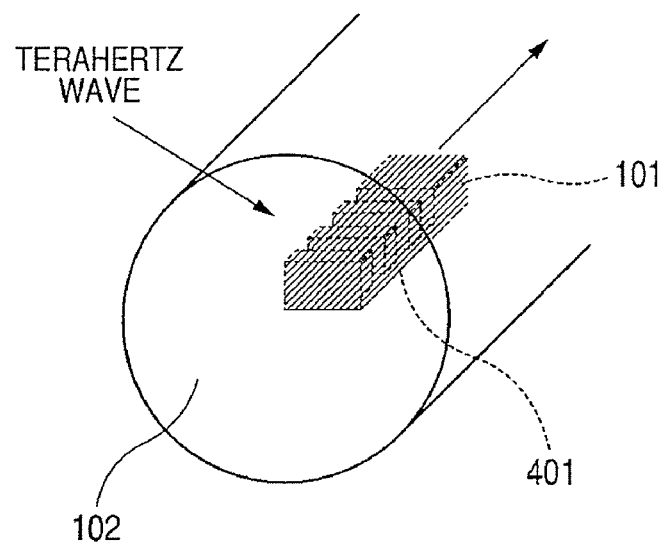
FIG. 4 is a schematic diagram showing an exemplary constitution of a coupling portion of the waveguide.

A case where the generation part 201 is constituted by means for generating a high frequency electromagnetic wave to propagate the electromagnetic wave into the space, and by coupling means to the waveguide 100, is considered. In this case, the coupling means is, for example, as shown in FIG. 4, constituted as a grating structure 401 formed in a part of the single line 101 constituting the waveguide 100. At this time, among high frequency electromagnetic waves propagated from the outside, the coupling means selectively couples the high frequency electromagnetic wave having the wavelength corresponding to the period of the grating. As a manufacturing method of this structure, for example, a method can be considered in which, for example, a single line 101 having the grating formed therein is inserted in a mold filled with a liquid dielectric member 102, and the dielectric member 102 is cured by heating. However, the manufacturing method of this structure is not limited to this method, and a known process technique can also be used.

Figure 5:
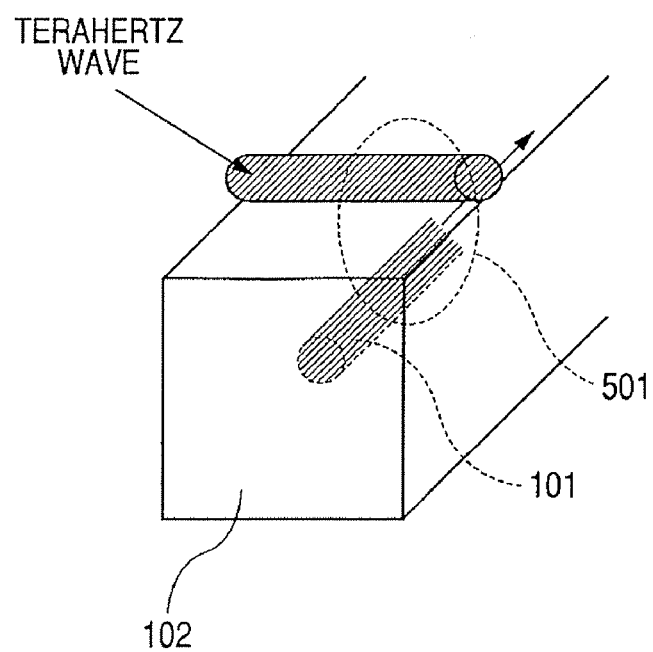
FIG. 5 is a schematic diagram showing another exemplary constitution of a coupling portion of the waveguide.

Further, as shown in FIG. 5, there is a method using a cross wire structure 501 in which a conductor as coupling means is further arranged to be orthogonal to the single line 101 constituting the waveguide 100. In this case, the high frequency electromagnetic waves propagated from the outside are coupled to the cross wire structure 501 similarly to the case described in the above described "Nature", vol. 432, p 376-379, 2004. As a manufacturing method of such a structure, for example, there is a method in which the cross wire structure 501 is patterned on the external peripheral surface of the dielectric member 102 including the single line 101. However, the manufacturing method of the structure is not limited to this manufacturing method, and a known process technique can also be used. Further, the cross wire structure 501 shown in FIG. 5 is produced on the external peripheral surface of the dielectric member 102, but may also be embedded into the dielectric member 102.

Figure 6:
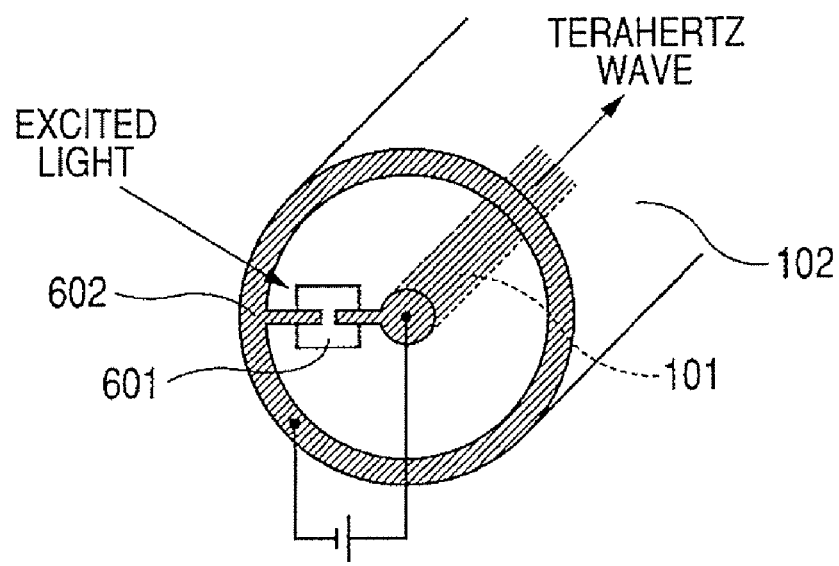
FIG. 6 is a schematic diagram showing another exemplary constitution of a coupling portion of the waveguide.

Further, the generation part 201 may also be constituted by integrating the means for generating the high frequency electromagnetic wave with the coupling means to the waveguide 100. In this case, for example, as shown in FIG. 6, there is a method in which a photoconductive switch structure 601 is used as the generation part 201. The photoconductive switch structure 601 is provided with a conductive member extracted from the single line 101 and a conductive member extracted from an electrode 602 which are separated at a minute gap. Further, the photoconductive switch structure 601 is constituted such that a semiconductor (for example, a low-temperature growth gallium arsenide: LT-GaAs) with a short carrier life time is brought into tight contact with the gap between the electrode extracted from the single line 101 and the electrode 602 formed in a part of the dielectric member 102. In the state where an electric field is applied to the above described gap portion, the photoconductive switch structure 601 is operated so as to generate a high frequency electromagnetic wave by being optically gated from the outside by the use of an ultra short pulse laser beam. The high frequency electromagnetic wave generated in the photoconductive switch structure 601 is coupled to the waveguide 100 constituted by the single line 101 and the dielectric member 102, and is propagated. These electrodes are patterned by a known process technique. Further, the semiconductor constituting the photoconductive switch structure 601 is, for example, formed to be thin and stuck to the dielectric member 102. The manufacturing method of the photoconductive switch structure 601 is not limited to this method. Further, in FIG. 6, the photoconductive switch structure 601 is formed on the end surface of the waveguide constituted by the single line 101 and the dielectric member 102, but is not limited to this structure. For example, the photoconductive switch structure 601 may also be formed in the inside of or on the external peripheral surface of the dielectric member 601. The electrode 602 is patterned concentrically around the single line 101. This is because by paying attention to the fact that the propagation mode of the waveguide 100 constituted by the single line 101 and the dielectric member 102 is a TEM mode which is the same as the coaxial cable, the structure of the high frequency electromagnetic wave generating side is formed into the coaxial structure in order to maintain a more excellent coupling state. However, what is important is that an electric field need only be applied across the gap between the conductors constituting the photoconductive switch structure 601. Thus, the photoconductive switch structure 601 is not naturally limited to this coaxial structure.

Figure 7:
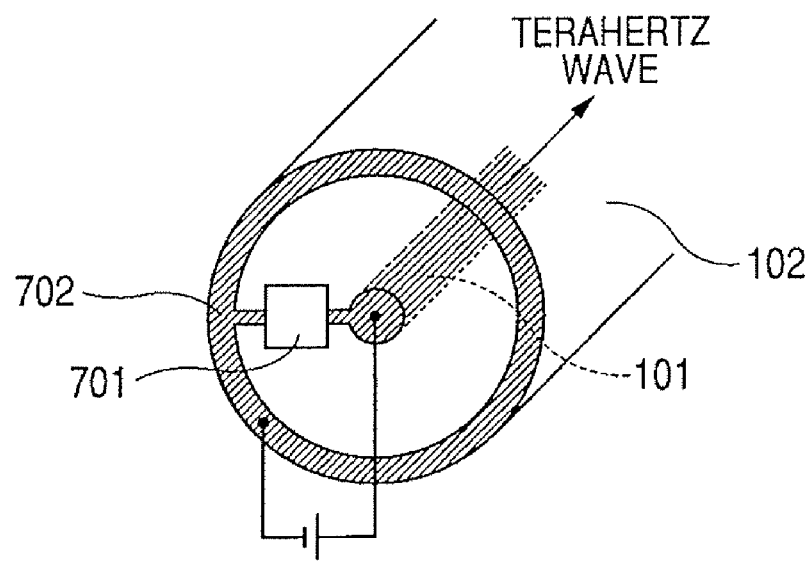
FIG. 7 is a schematic diagram showing another exemplary constitution of a coupling portion of the waveguide.

Further, as shown in FIG. 7, there is a method in which an electromagnetic wave gain structure 701 is used as the generation part 201. The electromagnetic wave gain structure 701 is constituted such that an electromagnetic wave gain substance having a gain in the high frequency electromagnetic wave region is brought into tight contact with an electrode drawn out from the single line 101 and an electrode 702 formed on a part of dielectric member 102, which electrodes are separated from each other at a minute gap. The electromagnetic wave gain substance is a semiconductor device which makes it possible to obtain the electromagnetic wave gain, as represented by, for example, a resonance tunnel diode (RTD), Gunn diode, and the like. Further, the electromagnetic wave gain substance may also be a high frequency electromagnetic wave oscillation device such as a quantum cascade laser. As described above, this electromagnetic wave gain substance is designed to obtain a gain at a desired frequency band of the high frequency electromagnetic waves. Accordingly, a high frequency electromagnetic wave is generated by applying a bias across the electromagnetic wave gain structure 701. Then, the high frequency electromagnetic wave generated by the electromagnetic wave gain structure 701 is coupled to the waveguide 100 constituted by the single line 101 and the dielectric member 102, and propagated through the waveguide. These electrodes are patterned by a known process technique. The electromagnetic wave gain structure 701 is, in FIG. 7, formed on the end surface of the waveguide 100 constituted by the single line 101 and the dielectric member 102, but is not limited to this constitution. For example, the electromagnetic wave gain structure 701 may also be formed in the inside of or on the external peripheral surface of the dielectric member 102. The electrode 702 is patterned concentrically around the single line 101. This is because by paying attention to the fact that the propagation mode of the waveguide 100 constituted by the single line 101 and the dielectric member 102 is a TEM mode which is the same as a coaxial cable, the structure of the high frequency electromagnetic wave generating side is formed into the coaxial structure in order to maintain a more excellent coupling state. However, what is important is that a bias need only be applied across the gap between the conductors constituting the electromagnetic wave gain structure 701. Thus, the electromagnetic wave gain structure 701 is not naturally limited to this coaxial structure.

Figure 8:
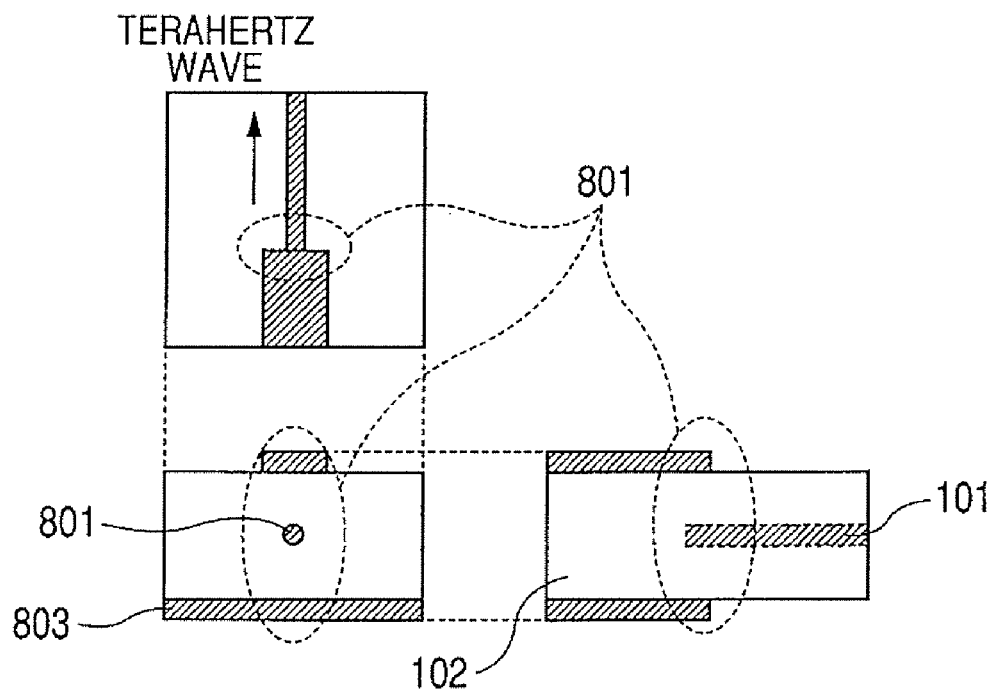
FIG. 8 is a schematic diagram showing another exemplary constitution of a coupling portion of the waveguide.

Further, as shown in FIG. 8, there is a method in which a waveguide conversion structure 801 is used as the generation part 201. The waveguide conversion structure 801 is constituted so as to couple the high frequency electromagnetic wave propagated in the other high frequency modules to the waveguide constituted by the single line 101 and the dielectric member 102. FIG. 8 shows a top view, a sectional view and a side view of this constitution. As shown in FIG. 8, the waveguide conversion structure 801 is constituted such that the single line 101 is inserted between a first conductor 802 and a second conductor 803 in the transmission line (microstrip line) constituted by the dielectric member 102, the first conductor 802 and the second conductor 803. With this constitution, the high frequency electromagnetic wave propagated in the high frequency module is coupled to the waveguide constituted by the single line 101 and the dielectric member 102 in the waveguide conversion structure 801, and is propagated. The transmission line structure constituting the waveguide conversion structure 801 is not limited to the microstrip line as shown in FIG. 8. For example, it is possible to use a transmission line structure, such as a coplanar waveguide, which is used for propagating high frequency electromagnetic wave signals. Further, three dimensional waveguide structures, such as a waveguide tube and a coaxial structure can also be applied. Further, in the waveguide conversion structure 801, it is also possible to consider a constitution in which the shapes of the single line 101 and the dielectric member 102 are partially changed in order to reduce the impedance mismatching and to improve the coupling state of high frequency electromagnetic wave signals. For example, at the end of the waveguide conversion structure 801, it is possible to consider to use a constitution in which the size of the single line 101 and the dielectric member 102 is partially increased or reduced, and a constitution in which the single line 101 and the dielectric member 102 have a tapered shape, or the like.

The constitution of the generation part 201 is not limited to these constitutions, and any constitution in which the high frequency electromagnetic wave generated in the generation part 201 is coupled to the waveguide 100 and propagated, may be used. For example, there is also a method for coupling the high frequency electromagnetic wave generated in the generation part 201 to the waveguide 100 via an antenna.

In FIG. 2, the detection part 202 has a function to detect the high frequency electromagnetic wave propagated through the waveguide 100. The same structure as that of the generation part 201 can be used as the structure of the detection part 202. However, the structure of the detection part 202 is not limited to these structures, and any structure which is capable of attaining the purpose of detecting the high frequency electromagnetic wave propagated through the waveguide 100, may be applied.

(Storage Means and Comparison Means of Sensor Device)

In the sensor device which measures physical properties of a specimen, reference information of the specimen is stored beforehand in the storage part 204. The reference information of the specimen stored in the storage part 204 include, for example, information of refractive index, attenuation, and the like. However, the reference information is not limited to these, and any information characterizing the physical properties of the specimen may be stored. The storage part 204 may also have a function to successively update the reference information of the specimen, which is stored in the storage part 204. For example, the information of physical properties of a specimen which is currently measured can also be stored as the reference information of the specimen.

The comparison part 203 is a part in which the information on the specimen detected by the detection part 202 is compared with the reference information stored in the storage part 204. The comparison part 203 has a function to process information on a specimen detected by the detection part 202 into a form corresponding to the reference information stored in the storage part 204. For example, the time series information is converted to the spectrum information. However, the processing form is not limited to this form. For example, the comparison part 203 may also have functions to obtain delay information or to calculate a complex dielectric constant. What is essential is that the comparison part 203 may only be a form capable of performing comparison with the reference information of specimen stored in the storage part 204.

The presentation part 205 presents the results of comparison performed by the comparison part 203. As a presenting method, a method for presenting on a display is conceivable. However, the presenting method is not limited to this method. For example, when only the presence of an inspection substance is to be known, methods for indicating by flashing of light and sound, or a tactile sense presentation device, and the like, can be used. What is essential is that the measurement results need only to be informed to the user by a certain method.

(Explanation of Operation of Sensor Device)

Next, the operation of the sensor device for measuring physical properties of a specimen, according to the present invention, is explained. First, a specimen is inserted in the gap of the waveguide 100 in the sensor device for measuring physical properties of the specimen, according to the present invention. The high frequency electromagnetic wave propagated through the waveguide 100 interacts with the specimen in the gap portion 103 of the waveguide 100. As a result, the propagation state of the high frequency electromagnetic wave propagated through the waveguide 100 is changed by the existence of the specimen. The change in the propagation state of the high frequency electromagnetic wave is different depending upon the physical properties of the specimen. The high frequency electromagnetic wave whose propagation state is changed is detected by the detection part 202.

Figure 3:
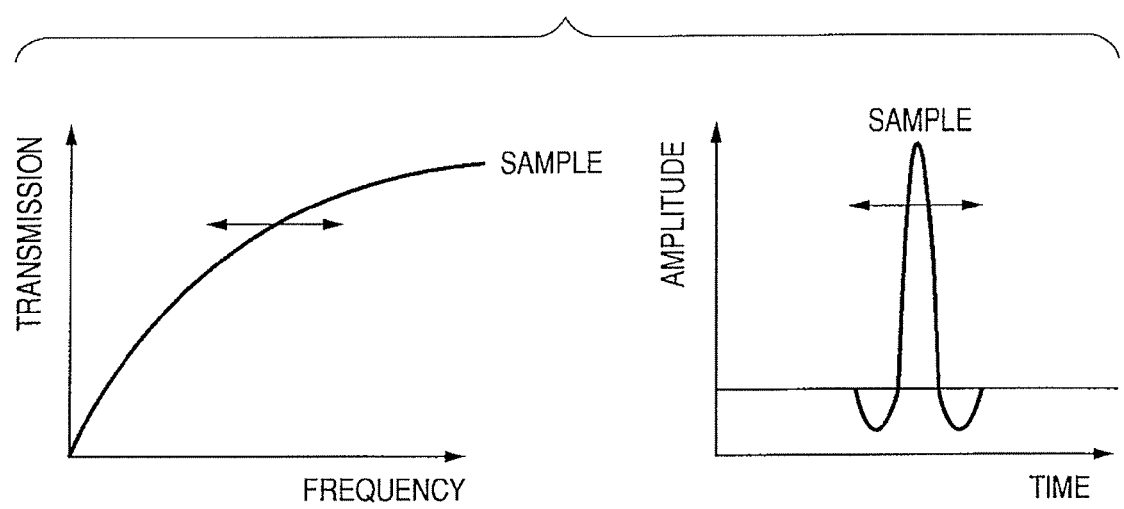
FIG. 3 is a graph for explaining an operation when the waveguide is used as an inspection element.

In FIG. 1, when the gap portion 103 exists in the dielectric member 102 of the waveguide 100, a capacitance component is added to the gap portion 103. This capacitance component is changed depending upon the physical properties of the specimen inserted in the gap portion 103. Therefore, when a specimen is inserted in the gap portion 103, the frequency characteristic and the propagation delay characteristic are changed as shown in FIG. 3. Here, FIG. 3 is an imaged graph showing the change in propagation characteristics, when a specimen is inserted in the gap portion 103. The figure shown here is only an imaged graph, and the propagation characteristics are actually changed in a more complicated manner by dispersion, attenuation and absorption characteristics of the specimen. As can been seen from the frequency characteristic in FIG. 3, it is anticipated that the waveguide 100 is made to function as a high pass filter which attenuates the signal at the low frequency side by the gap portion 103 of the waveguide 100. At this time, the cut-off frequency of the high pass filter is changed depending upon the physical properties of the specimen in the gap portion 103. Further, as can been seen from the propagation delay characteristic in FIG. 3, the delay time is changed depending upon the physical properties of the specimen. In the comparison part 203, the physical properties of the specimen are first obtained from the changes in the frequency characteristic and the propagation delay characteristic which are changed by inserting the specimen in the gap portion 103.

The physical property information of the specimen is stored beforehand in the storage part 204. Accordingly, it is possible to analyze and identify the specimen by comparing the physical property information stored in the storage part 204 with the obtained physical property information in the comparison part 203. In the sensor device for measuring the physical properties of the specimen according to the present invention, physical property information can be added to the storage part 204. For example, a specimen whose physical properties are known is measured beforehand by the sensor device for measuring physical properties of the specimen according to the present invention, and the measurement result is added to the storage part 204. The storage of such measurement results is effective to suppress variations in the measurement results which are intrinsic to the device.

These comparison results are presented to a measurer by the presentation part 205.

As described above, in the waveguide according to the present invention, the propagation state of the electromagnetic waves propagated through the waveguide can be changed, and thereby functional properties can be easily added to the waveguide. In the conventional transmission line technique, there is a problem in the loss and dispersion characteristics. Therefore, when a large scale circuit is to be formed, the problem causes signal deterioration, thereby making the control of the terahertz wave signal difficult. As described above, the waveguide according to the present invention is constituted such that functional properties are added to the waveguide of a single line which shows low-loss and low-dispersion characteristics, by means of a dielectric member. Accordingly, in the waveguide according to the present invention, the signal control can be performed while the influence of signal deterioration is kept to a minimum. As a result, it is possible to make the waveguide easily adapted for a large-scale circuit and device.

The sensor device for measuring physical properties of a specimen, according to the present invention, is constituted such that the specimen is inserted into the gap portion of the above described waveguide, and detects the change in the interaction with electromagnetic waves. Thus, the external mechanism, which is required for the conventional fiber waveguide and in which fiber waveguides are arranged opposite to each other via a certain gap, is not needed, and hence, the device constitution of the present invention can be simplified. Further, the loss and dispersion are comparatively large in the inspection apparatus using the conventional transmission line technique, and hence, it is desired that the inspection part and the detection part are arranged so as to be as close to each other as possible. However, the sensor device for measuring physical properties of a specimen, according to the present invention, is constituted so as to make an inspection part formed into the low-loss and low-dispersion waveguide structure, so that the inspection part and the detection part can be separated. Thereby, for example, when the inspection work is performed in a hazard area, it is possible that only the inspection part is carried into the hazard area and the detection work is performed in the safe area. This results in an effect to improve the safety. Further, since the inspection part can be separated, it is possible to perform an inspection work in a closed space (for example, in the inside of a chamber and the like), an inspection work in a solution, and the like. This results in an effect of expanding the applicable range of the inspection work.

EMBODIMENTS

In the following, more specific embodiments are described with reference to the drawings.

Embodiment 1

Figure 9:
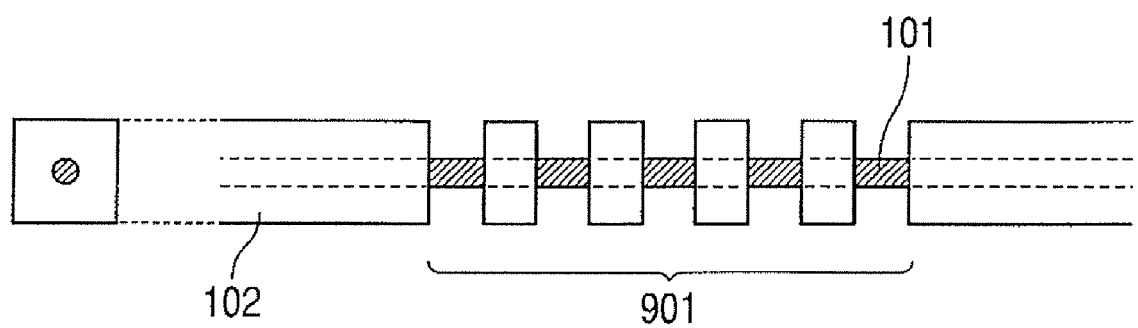
FIG. 9 is a schematic diagram showing an arrangement of a gap portion of a waveguide in Embodiment 1.

In the present embodiment, there is described a constitution example in which gap portions in a waveguide are periodically arranged. As shown in FIG. 9, a waveguide according to the present embodiment is constituted by a single line 101, a dielectric member 102, and a gap portion 901. As shown in FIG. 9, in the gap portion 901, gaps are periodically arranged. With such arrangement, the refractive index of the substance constituting the dielectric member 102 and the refractive index of the gap portion 901 are periodically changed. As a result, the waveguide according to the present embodiment has the wavelength selectivity resulting from a photonic band gap in the gap portion 901.

In the sensor device for measuring physical properties of a specimen, according to the present embodiment, the physical properties of the specimen are detected on the basis of the change in the wavelength selectivity.

In the present embodiment, a gold wire is used as the single line 101. High resistance silicon (dielectric constant: 11.4, conductivity: 0.01 S/m) is used as the dielectric member 102. However, the materials for the single line 101 and the dielectric member 102 are not limited to these materials. The single line 101 needs only to be a conductor. Thus, a platinum wire and a copper wire may also be used. As the dielectric member 102, any of dielectric materials may be used, but dielectric materials having low-dispersion and low-absorption characteristics to high frequency electromagnetic waves to be used are preferably used. Specifically, benzocyclobutene, polyimide, polysilane and the like are used as the dielectric material of the dielectric member 102. Further, a semiconductor material and the like may also be used as the dielectric material. In the present embodiment, as shown in FIG. 9, a cylindrical shape having a diameter of 10 µm is used as the shape of the single line 101. However, the shape of the single line 101 is not limited to this shape. For example, the shape of the single line 101 may be a polygonal shape. Further, the diameter of the single line 101 is not limited to this value. Further, as shown in FIG. 9, a square pole-shape having a side of 200 µm is used as the shape of the dielectric member 102. However, the shape of the dielectric member 102 is not limited to this shape. For example, a cylindrical shape and a polygonal shape may also be used. The length of one side of the dielectric member 102 is not limited to this value. This value is changed in accordance with the wavelength of the high frequency electromagnetic wave to be used.

As shown in FIG. 9, between the dielectric member 102, gaps are periodically arranged. The gap portions 901 having the width of 50 µm are periodically arranged at intervals of 50 µm. These gaps are constituted by removing the material constituting the dielectric member 102. Preferably, these gaps are periodically arranged at intervals of the order of wavelength corresponding to the effective wavelength of the electromagnetic wave propagated through the waveguide 100.

The waveguide used in the present embodiment is produced, for example, as follows. First, a groove for holding the single line 101 is produced in a high resistance silicon substrate having the thickness of 100 µm. Next, through holes having a size of 50 µm×200 µm are periodically produced so as to intersect perpendicularly to the groove for holding the above described single line 101. The through holes correspond to the gap portions 901. These patterns are produced such as by an ordinary photolithography technique, and a dry etching technique. Two substrates of this kind are produced. Then, the single line 101 is arranged in the groove portion of the substrate, which is then brought into tight contact with the other silicon substrate so as to make the groove portion face inwardly. In this case, a resin adhesive is applied to the interface of these silicon substrates, so as to make the substrates fixed with each other. Here, a resin adhesive having low-dispersion and low-absorption characteristics for the high frequency electromagnetic wave to be used is used. After the silicon substrates are fixed, the substrate is cut along the through hole so that a waveguide is formed. The manufacturing method is only an example, and the manufacturing method of the waveguide according to the present embodiment is not limited to this method. The process technique usually used can be used as the manufacturing method of the waveguide.

Figure 10:
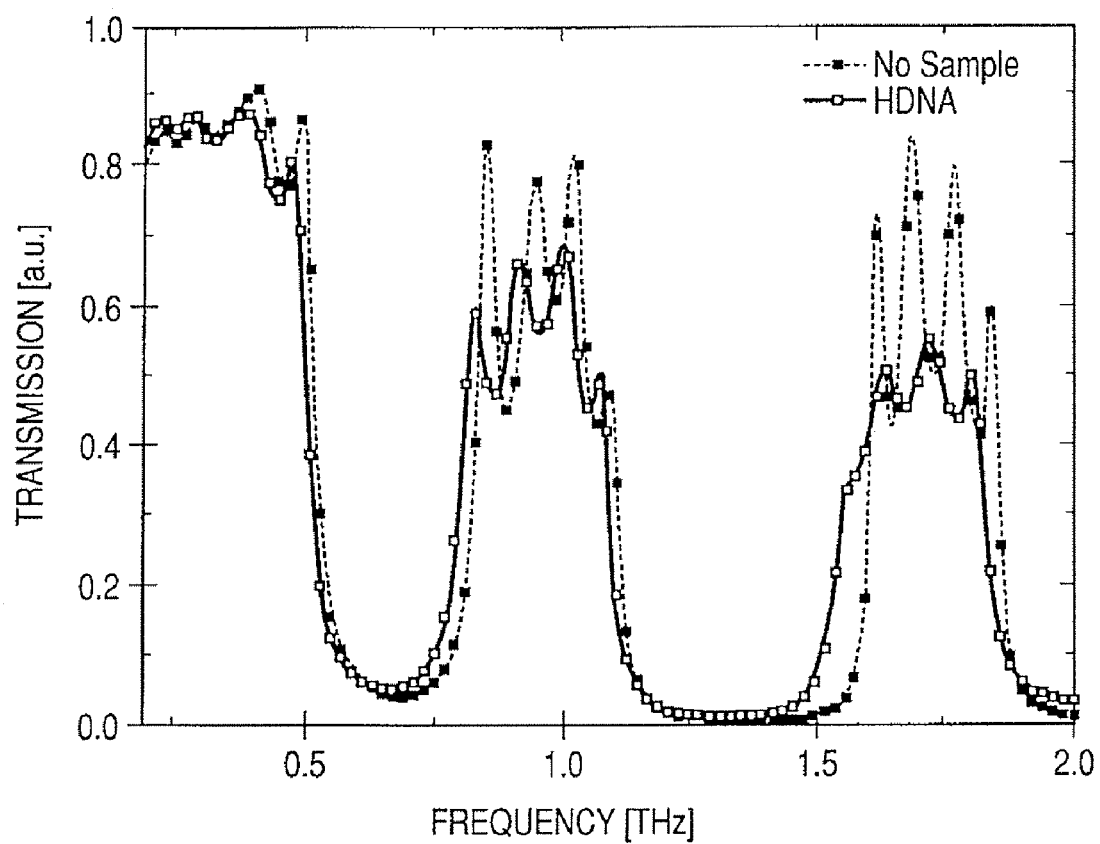
FIG. 10 is a graph showing the result of analysis for explaining an operation of an inspection element of Embodiment 1.

FIG. 10 is a graph showing an analysis result for explaining an operation when the waveguide according to the present embodiment is diverted to the sensor device for measuring physical properties of a specimen. FIG. 10 shows calculation results calculated by an electromagnetic field simulator.

In FIG. 10, the broken line shows a propagation characteristic in the state where there is no specimen in the gap portion 901 of the waveguide according to the present embodiment. Further, the solid line shows a propagation characteristic in the case where DNA (dielectric constant: 4.0, dielectric loss tangent (tan δ): 0.01) is inserted as a specimen into the gap portion 901 of the waveguide according to the present embodiment. As shown in FIG. 10, the gap portion 901 having the periodic arrangement of gaps causes non-transmission wavelength regions (wavelength regions where the level of transmission of electromagnetic waves is lowered to about 0) to be present. In addition, it is seen from the figure that when the specimen is inserted into the gap portion 901, the frequency characteristic is shifted to the low frequency side, as compared with the case where no specimen is inserted into the gap portion 901. Further, it is seen from the figure that the transmission intensity is also changed. Further, in DNA, since the dielectric constants are different between single stranded DNA and double stranded DNA, so that such difference can be detected. The physical properties of the specimen are acquired from this information. Further, although not shown in the figure, the delay information of high frequency electromagnetic waves propagated through the waveguide may also be used. When physical properties of a specimen are acquired, all of these kinds of information may be used, or any one of these kinds of information may also be selected. Also, a combination of these kinds of information may be used. Further, it is possible to detect the structural and characteristic changes of a specimen itself not only in DNA but also in biomolecules, such as protein and amino acid.

In connection with the physical properties of the specimen which are obtained in this way, the identification and analysis of the specimen are performed by comparing the obtained physical properties with information stored in the storage part 204.

In the present embodiment, the gap portion 901 of the waveguide is periodically arranged. It is generally known that such a structure represents a high Q value, and thereby the detection sensitivity is improved. That is, the sensor device for measuring physical properties of a specimen according to the present embodiment has not only the effect of enabling the high sensitivity measurement, but also the effect of enabling measurement with excellent sensitivity even for a trace of specimen.

Embodiment 2

Figure 11:
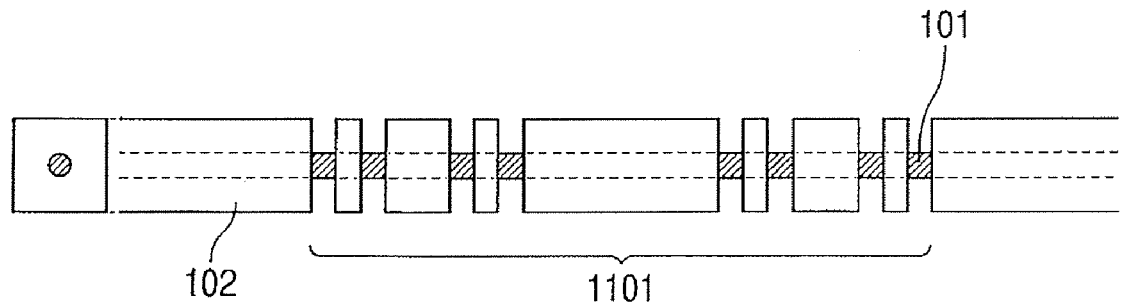
FIG. 11 is a schematic diagram showing an arrangement of a gap portion of a waveguide in Embodiment 2.

In the present embodiment, a constitution example in which the gap portions of the waveguide are self-similarly arranged is described. As shown in FIG. 11, the waveguide according to the present embodiment is constituted by a single line 101, a dielectric member 102 and gap portions 1101. As shown in the figure, the gap portions 1101 are self-similarly arranged. In the case of the present embodiment, the dielectric member 102 in the region corresponding to the gap portion 1101 is equally divided into three portions, and the central dielectric is left (which is referred to as one stage). The same procedure is repeated three times for each dielectric on both sides of the central dielectric, whereby, a structure (photonic fractal structure of three stages) is obtained. With this arrangement, a constitution in which the refractive index of the substance constituting the dielectric member 102 and the refractive index of the gap portion 1101 are self-similarly changed is obtained. As a result, the waveguide according to the present embodiment has the wavelength selectivity.

In the sensor device for measuring physical properties of a specimen according to the present embodiment, the physical properties of a specimen are detected by change in this wavelength selectivity.

In the present embodiment, a gold wire is used as the single line 101. High resistance silicon (dielectric constant: 11.4, conductivity: 0.01 S/m) is used as the dielectric member 102. In the present embodiment, as shown in FIG. 11, a cylindrical shape having a diameter of 10 µm is used as the shape of the single line 101. Further, as shown in FIG. 11, a square pole-shape having one side of 200 µm is used as the shape of the dielectric member 102. However, similarly to the case of Embodiment 1, the shapes of the single line 101 and the dielectric member 102 are not limited to these materials and shapes. As shown in FIG. 11, the gap portions 901 are self-similarly arranged in the dielectric member 102. For example, a case where an electromagnetic wave of about 1 THz is used as the high frequency electromagnetic wave to be used for the measurement is considered. At this time, as the gap portion 1101, the photonic fractal structure of three stages as described above is arranged in the region of the order of wavelength of the electromagnetic wave to be used. These gaps are constituted by removing the material constituting the dielectric member 102. Here, the order of wavelength means approximately one wavelength of the effective wavelength of the electromagnetic wave propagated through the waveguide 100.

In the present embodiment, the manufacturing method of the waveguide according to the present embodiment is the same as that shown in Embodiment 1.

In the case where a waveguide has a self-similar constitution as in the present embodiment, the propagation characteristic of the waveguide has a local mode in a certain specific frequency. Then, a case where this waveguide is diverted to a sensor device for measuring physical properties of a specimen is considered. When a specimen is inserted into the gap portion 1101 of the waveguide similarly to the case in Embodiment 1, the propagation state of the high frequency electromagnetic wave is changed, and thereby the frequency characteristic is changed. Specifically, the local mode is shifted to the low frequency side. Further, the transmission intensity is also changed similarly to the case in Embodiment 1. The physical properties of the specimen are obtained from these kinds of information. Further, the delay information of the high frequency electromagnetic wave propagated through the waveguide may also be used. When physical properties of a specimen are obtained, all of these kinds of information may be used, or any one of these kinds of information may be selected. Also, a combination of these kinds of information may be used. Further, similarly to the case in Embodiment 1, it is possible to detect structural and characteristic changes of the specimen itself, even by the sensor device for measuring the physical properties of the specimen according to the present embodiment.

The identification and analysis of the specimen are performed by comparing the physical properties of the specimen which are obtained in this way with information stored in the storage part 204.

Similarly to the case of Embodiment 1, it is generally known that the structure self-similarly formed as in the present embodiment represents a high Q value. Thereby, the detection sensitivity is improved. That is, the sensor device for measuring physical properties of a specimen according to the present embodiment has not only the effect that the high sensitivity measurement can be performed, but also the effect that the measurement with excellent sensitivity can be performed even for a trace of a specimen. Further, as described above, in the case where physical properties of a specimen are obtained on the basis of the change in the local mode, the propagation characteristic of a region surrounding the very sharp local mode shows a characteristic of preventing the electromagnetic wave from being propagated. This makes it possible to increase the S/N ratio of signals, and thereby a very small change in the frequency characteristics can also be measured. This results in an effect of improving the detection sensitivity of the specimen.

Embodiment 3

Figure 12:
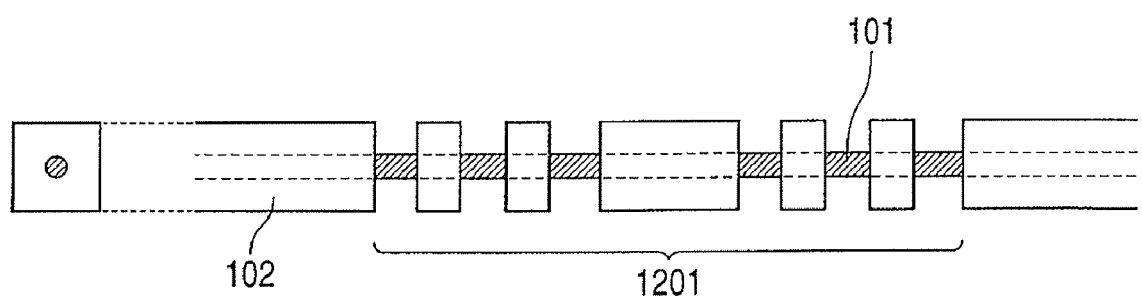
FIG. 12 is a schematic diagram showing an arrangement of a gap portion of a waveguide in Embodiment 3.

In the present embodiment, there is described a constitution example in which the gap portions of the waveguide are periodically arranged and an element for disturbing the periodicity is provided for a part of the periodically arranged gap portions. As shown in FIG. 12, the waveguide according to the present embodiment is constituted by a single line 101, a dielectric member 102, and gap portions 1201. As shown in the figure, the element for disturbing the periodicity of the gap portion 1201 is constituted by filling, with the dielectric member 102, a gap in a part of the periodic gap arrangement as described in Embodiment 1. However, the method for disturbing the periodicity is not limited to the method. For example, a method of filling a part of the gaps with a material different from the material constituting the dielectric member 102 is conceivable. Further, a method of disturbing the periodicity of the gap by changing the thickness of the member constituting the gap portion or by changing the interval of the gaps is also conceivable. These arrangements cause the periodic change in the refractive indexes of the substance constituting the dielectric member 102 and of the gap portions 1201 to be partially disturbed in the gap portions 1201. As a result, the waveguide according to the present embodiment has the wavelength selectivity resulting from a photonic band gap in the gap portion 1201, and has a local mode in the photonic band gap.

In the sensor device for measuring physical properties of a specimen, according to the present embodiment, the physical properties of the specimen are detected by change in the wavelength selectivity.

In the present embodiment, the shape of the single line 101 and the dielectric member 102 is the same as those of the embodiments as described above.

As shown in FIG. 12, the gap portion 1201 is periodically arranged in the dielectric member 102, and the gap in the central portion is filled with the material constituting the dielectric member 102. In this way, the element for disturbing the periodicity is constituted by filling a part of the gaps. These gaps are constituted by removing the material constituting the dielectric member 102.

In the present embodiment, the manufacturing method of the waveguide according to the present embodiment is the same as that of the embodiments as described above.

Figure 13:
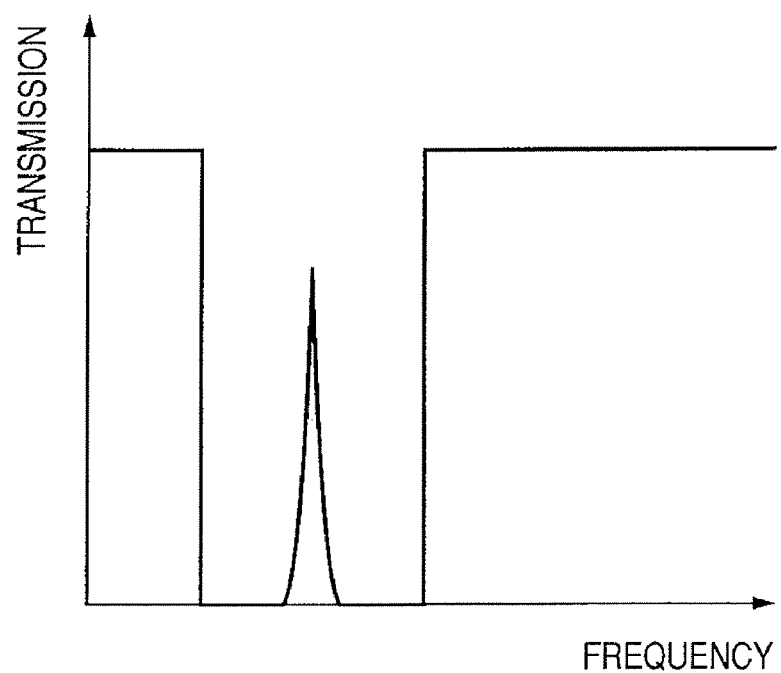
FIG. 13 is an imaged graph of the propagation characteristic of the waveguide in Embodiment 3.

FIG. 13 is an imaged graph of the propagation characteristic in the case where the waveguide according to the present embodiment is diverted to the sensor device for measuring physical properties of a specimen. As shown in FIG. 13, the propagation characteristic of the waveguide according to the present embodiment has a local mode in the band gap. Then, a case where this waveguide is diverted to the sensor device for measuring physical properties of a specimen is considered. Similarly to the embodiments as described above, when a specimen is inserted into the gap portion 1201 of the waveguide, the propagation state of the high frequency electromagnetic wave is changed, and thereby the frequency characteristic is changed. Specifically, the band gap and the local mode are shifted to the low frequency side. Further, the transmission intensity is also changed, similarly to the cases of the embodiments as described above. The physical properties of the specimen are obtained from these kinds of information. Further, although not shown in the figure, the delay information of the high frequency electromagnetic wave propagated through the waveguide may also be used. When physical properties of a specimen are obtained, all of these kinds of information may be used, or any one of these kinds of information may be chosen. Also, a combination of these kinds of information may be used. Further, as described above, it is possible to detect structural and characteristic changes of the specimen itself, even by the sensor device for measuring the physical properties of the specimen according to the present embodiment.

The identification and analysis of the specimen are performed by comparing the physical properties of the specimen which are obtained in this way, with the information stored in the storage part 204.

Similarly to the case of the embodiments as described above, it is generally known that the waveguide according to the present embodiment, which is constituted so as to be similar to the periodic constitution, represents a high Q value. Thereby, the detection sensitivity is improved. That is, the sensor device for measuring physical properties of a specimen according to the present embodiment has not only the effect that the high sensitivity measurement can be performed, but also the effect that the measurement with excellent sensitivity can be performed even for a trace of the specimen. Further, as shown in FIG. 13, in the case where physical properties of a specimen are obtained by change in the local mode, the propagation characteristic in the region surrounding the very sharp local mode shows a characteristic of preventing the electromagnetic wave from being propagated. This makes it possible to increase the S/N ratio of signals and thereby a very small change in the frequency characteristic can also be measured. This results in an effect of improving the detection sensitivity of the subject.

Embodiment 4

In the present embodiment, there is shown an example in which the sensor device for measuring physical properties of a specimen is applied for a sensor device for measuring physical properties of a specimen in a solution.

Figure 14:
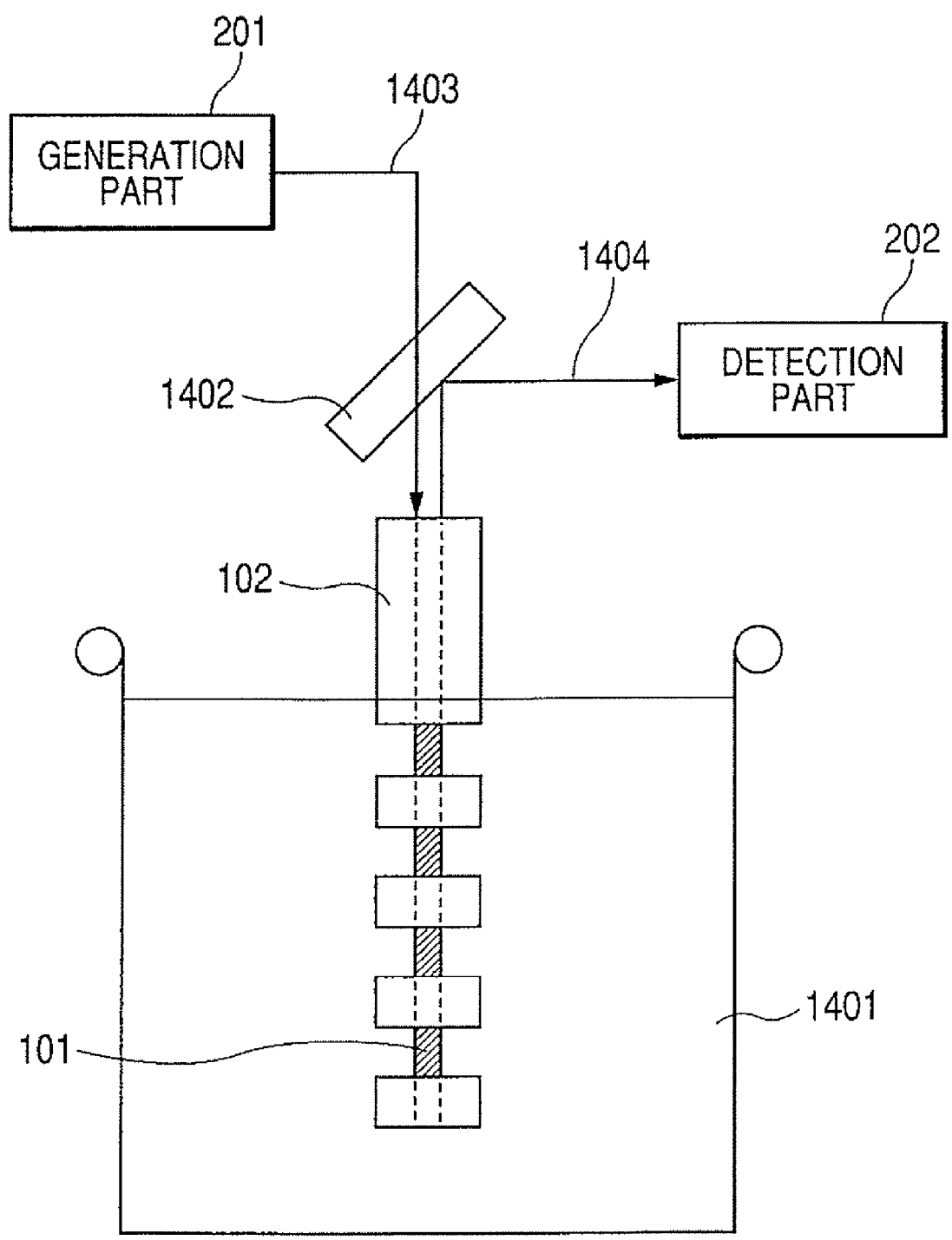
FIG. 14 is a schematic diagram of a measuring apparatus of Embodiment 4.

FIG. 14 is a schematic diagram showing a detection part for a specimen in a measuring device according to the present embodiment. As shown in FIG. 14, the measuring device according to the present embodiment is constituted by a generation part 201 which generates a terahertz wave, a half mirror 1402, a detection part 202, a single line 101 and a dielectric member 102. The dielectric member 102 has gap portions. As described above, the low-loss and low-dispersion waveguide is constituted by the single line 101 and the dielectric member 102, so that a part having the gap portion serves as a sensor part.

As described above, in the waveguide according to the present invention, the high frequency electromagnetic wave propagated through the waveguide is confined in the inside of the dielectric member. Accordingly, even when the substance outside the waveguide is changed, the propagation characteristic of the high frequency electromagnetic wave is not changed. Therefore, for example, the propagation characteristic of the high frequency electromagnetic wave is not changed in a solution and in various kinds of external atmosphere.

In the present embodiment, it is assumed that the above described gap portion is arranged in the same periodic manner as that of Embodiment 1. Thus, the waveguide according to the present embodiment has the wavelength selectivity resulting from the photonic band gap. However, as described above, the arrangement of the gap portions is not limited to this arrangement. The high frequency electromagnetic wave propagated through the waveguide interacts with the external substance in the gap portion. The waveguide according to the present embodiment has a stub shape as shown in FIG. 14. Therefore, the incident high frequency electromagnetic wave 1403 propagated through the waveguide is reflected at the end surface of the waveguide, and the reflected high frequency electromagnetic wave 1404 is propagated. A processing for making the electromagnetic wave efficiently reflected may be applied to the end surface of the waveguide according to the present embodiment. For example, a method of coating the end surface of the waveguide with a metal is conceivable in order to enable the electromagnetic wave to be efficiently reflected. However, the method for enabling the electromagnetic wave to be efficiently reflected is not limited to this method.

The half mirror 1402 has a function of branching the incident high frequency electromagnetic wave 1403 incident on the waveguide according to the present embodiment as well as the reflected high frequency electromagnetic wave 1404 reflected from the waveguide. Therefore, any means having this branching function is not limited to the half mirror. The other means may be used, provided that the means have such a branching function. For example, the means having the branching function can also be constituted such as by a coupler, circulator, in which a wave guide tube and the like is used.

The reflected high frequency electromagnetic wave 1404 is detected by the detection part 202. Then, by the comparison part 203 and the storage part 204 (which are not shown), the physical properties of the specimen are detected so as to enable the specimen to be identified and analyzed.

The operation is explained. First, the waveguide constituted by the single line 101 and the dielectric member 102 is inserted into an inspection solution 1401. Thereby, the gap portion of the dielectric member 102 is filled with the inspection solution 1401. Next, the incident high frequency electromagnetic wave 1403 used for detection is emitted to the space by the generation part 201. The incident high frequency electromagnetic wave 1403 is made incident on the half mirror 1402 by a spatial optical system (not shown). The half mirror 1402 transmits the incident high frequency electromagnetic wave 1403. The transmitted incident high frequency electromagnetic wave 1403 is coupled to the waveguide by the waveguide coupling means (not shown) and is propagated.

In the above, the generation part 201 is explained as a part also serving the waveguide coupling means. However, in the present embodiment, in order to clearly explain the means (for example, the half mirror 1402) for branching the electromagnetic wave, the generation part is separately explained from the branching means.

The incident high frequency electromagnetic wave 1403 that propagates the high frequency electromagnetic wave interacts with the inspection solution 1401 in the gap portion, so that the propagation characteristic of the high frequency electromagnetic wave is changed. Then, the high frequency electromagnetic wave is reflected at the end surface of the waveguide and becomes the reflected high frequency electromagnetic wave 1404. The reflected high frequency electromagnetic wave 1404 is taken out to the outside by the waveguide coupling means (not shown). Then, the reflected high frequency electromagnetic wave 1404 is reflected by the half mirror 1402 in the direction different from the direction of the propagation path of the incident high frequency electromagnetic wave 1403. This reflected high frequency electromagnetic wave 1404 is detected by the detection part 202. Then, by the comparison part 203 and the storage part 204 (which are not shown), the physical properties of the specimen are detected, so that the specimen is identified and analyzed. The specific detecting operation of the present embodiment is the same as that of the above described embodiments, and hence, the explanation of the detecting operation of the present embodiment is omitted.

In the present embodiment, the high frequency electromagnetic wave is handled by using the spatial optical system, but the method for handling the high frequency electromagnetic wave is not limited to this form. For example, it is possible to replace the spatial optical system with a waveguide, and to make the spatial optical system into a modular or integrated form by using a waveguide structure. Further, in the present embodiment, a specimen in a solution is detected, but the specimen is not limited to this. The physical properties of the gap portion in the dielectric member 102 need only to be changed. Thus, for example, the present embodiment can also be used for the detection of a specimen in an atmosphere, powder or soil.

The present embodiment is an embodiment of inserting the inspection portion of the sensor device for measuring physical properties of a specimen into the specimen to be inspected. Therefore, as described above, the step for filling the inspection portion with the specimen can be simplified. Although an external mechanism is used for filling the specimen in the prior art, the mechanism can be eliminated in the present invention, and thereby the device can be simplified. When the inspection object is a hazardous material, the step of handling the hazardous material can be simplified, thereby obtaining an effect of improving the safety.

This application claims the benefit of Japanese Patent Application No. 2005-256655, filed Sep. 5, 2005, which is hereby incorporated by reference herein in its entirety.

The invention claimed is:

1. A waveguide comprising:
  a single line formed by a conductive material for propagating an electromagnetic wave including at least a part of a frequency band of 30 GHz or more and 30 THz or less;
  a first dielectric member covering the single line; and
  a second dielectric member covering the single line, with a gap portion between the first dielectric member and the second dielectric member,
  wherein the electromagnetic wave which propagates from the single line covered by the first dielectric member to the single line covered by the second dielectric member, when propagating through the single line at the gap portion, is interactable with a specimen to be disposed at the gap portion.

2. The waveguide according to claim 1, wherein the gap portion is configured such that a refractive index with respect to the electromagnetic wave propagating through the single line is changed.

3. The waveguide according to claim 2, wherein the gap portion has a plurality of gaps in a regular manner.

4. The waveguide according to claim 3, wherein the regular manner is a periodic manner or a self-similar manner.

5. The waveguide according to claim 4, wherein the regularity of the plurality of gaps are set in wavelength order of the electromagnetic wave.

6. A device for detecting physical properties of a specimen, comprising:
  a waveguide comprising:
  a single line formed by a conductive material for propagating an electromagnetic wave including at least a part of a frequency band of 30 GHz or more and 30 THz or less;
  a first dielectric member covering the single line; and
  a second dielectric member covering the single line with a gap portion between the first dielectric member and the second dielectric member,
  wherein the electromagnetic wave which propagates from the single line covered by the first dielectric member to the single line covered by the second dielectric member, when propagating through the single line at the gap portion, is interactable with a specimen to be disposed at the gap portion; and
  a detector to detect the electromagnetic wave which has propagated through the single line covered by the second dielectric member.

7. The device according to claim 6, further comprising a storage part for storing information of physical properties of the specimen, wherein the specimen is identified by comparing the information stored in the storage part with information based on a change in the propagation state of the electromagnetic wave which is influenced and changed by the specimen when the specimen exists in the vicinity of the gap portion.

8. A waveguide comprising:
  a conductor for propagating an electromagnetic wave including at least a part of a frequency band of 30 GHz or more and 30 THz or less;
  a first dielectric member which covers the conductor; and
  a second dielectric member which covers the conductor with a gap portion between the first dielectric member and the second dielectric member,
  wherein the electromagnetic wave which propagates from the conductor covered by the first dielectric member to the conductor covered by the second dielectric member, when propagating through the conductor at the gap portion, is interactable with a specimen to be disposed at the gap portion.

9. The waveguide according to claim 1, wherein the gap portion constitutes at least a part of the single line.

* * * * *